(12) United States Patent
Ahlers et al.

(10) Patent No.: US 6,639,114 B2
(45) Date of Patent: Oct. 28, 2003

(54) HYDROFORMYLATION CATALYST COMPRISING A COMPLEX WITH LIGANDS HAVING A STRUCTURE DERIVED FROM BISPHENOL A

(75) Inventors: Wolfgang Ahlers, Worms (DE); Rocco Paciello, Bad Dürkheim (DE); Dieter Vogt, Eindhoven (DE); Jarl Ivar van der Vlugt, Eindhoven (NL)

(73) Assignee: BASF Aktiengesellschaft, Ludwigshafen (DE)

( * ) Notice: Subject to any disclaimer, the term of this patent is extended or adjusted under 35 U.S.C. 154(b) by 29 days.

(21) Appl. No.: 10/073,327

(22) Filed: Feb. 13, 2002

(65) Prior Publication Data

US 2002/0111517 A1 Aug. 15, 2002

(30) Foreign Application Priority Data

Feb. 13, 2001 (DE) .......................... 101 06 481

(51) Int. Cl.[7] .................. C07C 45/49; C07C 41/00; C07C 321/00; C07F 9/02; B01J 31/00
(52) U.S. Cl. .................. 568/444; 568/451; 568/480; 568/633; 568/638; 568/17; 568/21; 568/22; 502/162
(58) Field of Search .................. 568/444, 451, 568/480, 633, 638, 17, 21, 22; 502/162

(56) References Cited

U.S. PATENT DOCUMENTS

| | | | |
|---|---|---|---|
| 4,694,109 A | 9/1987 | Devon et al. ............. 568/454 |
| 4,755,624 A | 7/1988 | Phillips et al. ........... 568/454 |
| 4,851,581 A | 7/1989 | Devon et al. ............. 568/17 |
| 4,904,808 A | 2/1990 | Devon et al. ............. 556/21 |
| 5,332,846 A | 7/1994 | Devon et al. ............. 556/21 |
| 5,696,297 A | * 12/1997 | Kneuper et al. | |
| 5,710,344 A | * 1/1998 | Breikss et al. | |
| 6,342,605 B1 | 1/2002 | Geissler et al. ........... 546/22 |
| 6,486,359 B1 | * 11/2002 | Maas et al. | |

FOREIGN PATENT DOCUMENTS

| | | |
|---|---|---|
| DE | 198 27 232 | 12/1999 |
| WO | WO 95/30680 | 11/1995 |
| WO | WO 98/43935 | 10/1998 |

OTHER PUBLICATIONS

Van der Veen et al. "New phosphacyclic Diphosphines for Rhodium–Catalyzed Hydroformylation" Oganomteallics vol. 18, (1999) pp. 4677–4777.
Kranenburg et al. "New Diphosphine Ligands Based on Heterocyclic Aromatics Inducing Very High Regioselectivity in Rhodium–Catalyzed Hydroformylation: Effect of the Bite Angle" Organometallics vol. 14 (1995) pp. 3081–3089.
Selent et al. "Novel Oxyfunctionalized Phosphonite Ligands of the Hydroformylation of Isomeric n–olefins" Anges. Chem Intl Ed. vol. 39 (2000) pp. 1639–1641.
Arena et al. "Formation of Met allamacrocycles from Palladium(II), Platinum(II) and Copper(I) Complexes and the Ditopic Ligands [{p–(Ph$_2$PO)C$_6$H$_4$}$_2$CMe$_2$], [{2–Ph$_2$PO–3, 5–(Me$_3$C)$_2$C$_6$H$_2$]S], [{p–[(C$_{10}$H$_6$O)$_2$PO]C$_6$H$_4$}$_2$CMe$_2$]" Eur. J. Inorg. Chem. (2001) pp. 247–255.

* cited by examiner

Primary Examiner—Samuel Barts
Assistant Examiner—Sikarl A. Witherspoon
(74) Attorney, Agent, or Firm—Keil & Weinkauf

(57) ABSTRACT

Ethylenically unsaturated compounds are hydroformylated in the presence of a hydroformylation catalyst comprising at least one complex of a metal of transition group VIII with at least one phosphorus-containing compound as ligand, where this compound contains two groups which contain P atoms and are bound to a molecular skeleton derived from bisphenol A.

9 Claims, No Drawings

HYDROFORMYLATION CATALYST COMPRISING A COMPLEX WITH LIGANDS HAVING A STRUCTURE DERIVED FROM BISPHENOL A

The present invention relates to a process for the hydroformylation of ethylenically unsaturated compounds, in which the hydroformylation catalyst used comprises at least one complex of a metal of transition group VIII with at least one phosphorus-containing compound as ligand, where this compound in each case comprises two groups containing P atoms and bound to a molecular skeleton derived from bisphenol A. The invention further relates to novel compounds of this type and catalysts comprising at least one complex of a metal of transition group VIII with at least one such compound as ligand.

Hydroformylation or the oxo process is an important industrial process and is employed for preparing aldehydes from olefins, carbon monoxide and hydrogen. These aldehydes can, if desired, be hydrogenated by means of hydrogen in the same process to produce the corresponding oxo alcohols. The reaction itself is strongly exothermic and generally proceeds under superatmospheric pressure and at elevated temperatures in the presence of catalysts. Catalysts used are Co, Rh, Ir, Ru, Pd or Pt compounds or complexes which may be modified with N- or P-containing ligands to influence the activity and/or selectivity. Owing to the possible addition of CO at each of the two carbon atoms of a double bond, the hydroformulation reaction results in the formation of mixtures of isomeric aldehydes. In addition, it is possible for double bond isomerization, i.e., a shift of internal double bonds to a terminal position and vice versa, to occur.

Owing to the considerably greater industrial importance of α-aldehydes, optimization of the hydroformylation catalysts so as to achieve a very high hydroformylation activity combined with a very low tendency to form aldehyde groups which are not in the α position is desirable. In addition, there is a need for hydroformylation catalysts which lead to good yields of α-aldehydes, in particular n-aldehydes, even when internal linear olefins are used as starting materials. Here, the catalyst has to make possible the establishment of an equilibrium between internal and terminal double bond isomers and also very selectively catalyze the hydroformylation of the terminal olefins.

The use of phosphorus-containing ligands for stabilizing and/or acvtivating the catalyst metal in rhodium-catalyzed low-pressure hydroformylation is known. Suitable phosphorus-containing ligands are, for example, phosphines, phosphinites, phosphonites, phosphites, phosphoramidites, phospholes and phosphabenzenes. The most widely used ligands at present are triarylphosphines, e.g. triphenylphosphine and sulfonated triphenylphosphine, since these have sufficient stability under the reaction conditions. However, these ligands suffer from the disadvantage that very high excesses of ligands are generally necessary to achieve satisfactory yields, particularly of linear aldehydes.

In Eur. J. Inorg. Chem. 2001, 247–255, C. G. Arena et al. describe metallamacrocycles of Pd, Pt and Cu complexes of the ligands [{p-(Ph$_2$PO)C$_6$H$_4$}$_2$CMe$_2$], [{2-Ph$_2$PO-3,5-(Me$_3$C)$_2$C$_6$H$_2$}$_2$S] and [{p-[(C$_{10}$H$_6$O)$_2$PO]C$_6$H$_4$}$_2$CMe$_2$]. Use in hydroformylation is not described.

In Angew. Chem. Int. Ed. 39, 1639 (2000), D. Selent et al. describe the isomerizing hydroformylation of internal olefins in the presence of rhodium catalysts in which oxy-functionalized bisphenylmonophosphonites are used as ligands. A disadvantage of these catalysts is their low n-selectivity. Thus, the hydroformylation of isomeric n-octenes gave n-nonanal in a yield of not more than 47.9%.

WO-A-98/43935 describes the use of chelating ligands in catalysts for hydroformylation.

In Organometallics 1995, 14, pp. 3081–3089, M. Kranenburg et al. describe chelating phosphines such as bis(2-(diphenylphosphino)-phenyl) ether and ones having a xanthene skeleton and their use for regioselective rhodium-catalyzed hydroformylation. A disadvantage of these chelating phosphines is that they are not suitable for the isomerizing hydroformylation of internal olefins with high α- or n-selectivity.

In Organometallics 1999, 18, pp. 4765–4777, van der Veen et al. describe the use of phosphacyclic diphosphines having a xanthene skeleton as ligands for rhodium-catalyzed hydroformylation. A disadvantage of these catalysts is their very low activity which makes their use in industrial processes uneconomical.

WO 95/30680 describes bidentate phosphine ligands in which the phosphorus atoms are bridged by ortho-fused ring systems comprising two aryl groups and also describes the use of these ligands in catalysts for hydroformylation. A disadvantage of these catalysts is that they are not suitable for the isomerizing hydroformylation of internal olefins with good α- or n-selectivity.

EP-A-0982314 describes bidentate carbocyclic or heterocyclic phosphine ligands and a process for preparing linear aldehydes by hydroformylation of internal olefins using such ligands. A disadvantage of these ligands is their very low activity which makes their use in industrial processes uneconomical.

DE-A-19827232 describes catalysts based on monodentate, bidentate or polydentate phosphinite ligands in which the phosphorus atom and oxygen atom of the phosphinite group are part of a 5- to 8-membered heterocycle and also describes their use for hydroformylation and hydrocyanation. The bidentate ligands can, inter alia, have a xanthene skeleton. A disadvantage of these ligands is that the α- or n-selectivity in the isomerizing hydroformylation of internal olefins is in need of improvement.

U.S. Pat. No. 4,694,109, No. 4,755,624, No. 4,851,581 and No. 4,904,808 describe chelating ligands for hydroformylation which have a skeleton based on two aryl groups bound directly to one another via a single bond.

U.S. Pat. No. 5,332,846 describes bisphosphines in which two phosphine groups are bound via substituted or unsubstituted methylene groups to a molecular skeleton comprising two arylene groups joined via a single bond. These are suitable as ligands for hydroformylation catalysts.

The unpublished German patent application P 100 05 794.2 describes compounds of phosphorus, arsenic and antimony based on diaryl-fused bicyclo[2.2.n] skeletons and their use as ligands for hydroformylation catalysts.

The unpublished German patent application P 100 46 026.7 describes a hydroformylation process in which the catalyst used comprises at least one complex of a metal of transition group VIII with at least one phosphorus-, arsenic- or antimony-containing compound having a xanthene-like molecular skeleton as ligand.

The unpublished German patent applications 100 23 471.2 and 101 01 939.4 describe a hydroformylation process in which the hydroformylation catalyst used is a complex of a metal of transition group VIII with at least one ligand comprising two triaryl groups, where each of the triaryl groups comprises a phosphorus-, arsenic- or antimony-containing radical and one aryl radical of each of the two triaryl groups is bound via a single bond to a nonaromatic 3- to 8-membered carbocyclic or heterocyclic bridging group.

None of the abovementioned documents describes phosphorus-containing compounds having a skeleton derived from bisphenol A and their use as ligands in hydroformylation catalysts.

It is an object of the present invention to provide an improved process for the hydroformylation of compounds which contain at least one ethylenically unsaturated double bond. In the hydroformylation of α-olefins, it should preferably achieve a very high proportion of α-aldehydes or α-alcohols (α-selectivity). In particular, the process should be suitable for the hydroformylation of internal linear olefins with high regioselectivity to terminal product aldehydes. A further object of the invention is to provide novel compounds and novel catalysts which comprise at least one complex of a metal of transition group VIII with such a compound as ligand.

We have found that this object is achieved by a hydroformylation process in which the hydroformylation catalyst used comprises at least one complex of a metal of transition group VIII with at least one phosphorus-containing compound as ligand. This compound contains at least two groups containing a P atom and each of the two groups is bound to a different phenyl ring of a molecular skeleton derived from bisphenol A.

The present invention accordingly provides a process for the hydroformylation of compounds containing at least one ethylenically unsaturated double bond by reaction with carbon monoxide and hydrogen in the presence of a hydroformylation catalyst comprising at least one complex of a metal of transition group VIII with at least one ligand selected from among compounds of the formula I

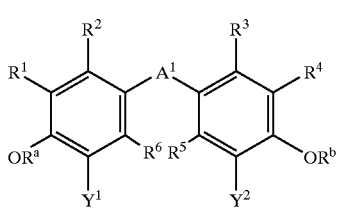

(I)

where $A^1$ is O, S, $NR^c$, $SiR^dR^e$ or $CR^fR^g$, where
$R^c$, $R^d$, $R^e$, $R^f$ and $R^g$ are each, independently of one another, hydrogen, alkyl, cycloalkyl, heterocycloalkyl, aryl or hetaryl, where $R^f$ and $R^g$ together with the carbon atom to which they are bound may also form a 3- to 8-membered carbocycle or heterocycle which may additionally be fused with one, two or three cycloalkyl, heterocycloalkyl, aryl and/or hetaryl groups, $Y^1$ and $Y^2$ are, independently of one another, radicals containing at least one phosphorus atom, $R^a$ and $R^b$ are, independently of one another, hydrogen, alkyl, cycloalkyl, heterocycloalkyl, aryl, hetaryl or $(CHR^iCH_2O)_xR^h$, where $R^h$ is hydrogen, alkyl, cycloalkyl or aryl, $R^i$ is hydrogen, methyl or ethyl and x is an integer from 1 to 120, and $R^1$, $R^2$, $R^3$ $R^4$, $R^5$ and $R^6$ are each, independently of one another, hydrogen, alkyl, cycloalkyl, heterocycloalkyl, aryl, hetaryl, $COOR^h$, $COO^-M^+$, $SO_3R^h$, $(SO_3)^-M^+$, $NE^1E^2$, $NE^1E^2E^{3+}X^-$, alkylene-$NE^1E^2E^{3+}X^-$, $OR^h$, $SR^h$, $(CHR^iCH_2O)_xR^h$, $(CH_2N(E^1))_xR^h$, $(CH_2CH_2N(E^1))_xR^h$, halogen, trifluoromethyl, nitro, acyl or cyano, where $R^h$, $E^1$, $E^2$ and $E^3$ are identical or different radicals selected from among hydrogen, alkyl, cycloalkyl and aryl, $R^i$ is hydrogen, methyl or ethyl,
$M^+$ is a cation,
$X^-$ is an anion and
x is an integer from 1 to 120, or
$R^1$ and $R^2$ and/or $R^3$ and $R^4$ together with the adjacent carbon atoms of the benzene ring to which they are bound form a fused ring system comprising 1, 2 or 3 further rings.

For the purposes of the present invention, the expression 'alkyl' encompasses both straight-chain and branched alkyl groups. The alkyl groups are preferably straight-chain or branched $C_1$–$C_8$-alkyl groups, more preferably $C_1$–$C_6$-alkyl groups and particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

The expression alkyl also encompasses substituted alkyl groups. Substituted alkyl groups preferably bear 1, 2, 3, 4 or 5, in particular 1, 2 or 3 substituents, preferably selected from among cycloalkyl, heterocycloalkyl, aryl, hetaryl, halogen, $NE^1E^{23}$, $(NE^1E^2E^3)^+$, carboxyl, carboxylate, $—SO_3H$ and sulfonate.

The expression cycloalkyl encompasses unsubstituted and substituted cycloalkyl groups. A cycloalkyl group is preferably a $C_4$–$C_8$-cycloalkyl group and in particular a $C_5$–$C_7$-cycloalkyl group such as cyclopentyl, cyclohexyl or cycloheptyl.

If the cycloalkyl group is substituted, it preferably bears 1, 2, 3, 4 or 5, in particular 1, 2 or 3, substituents selected from among alkyl, alkoxy and halogen.

Heterocycloalkyl is preferably pyrrolidinyl, tetrahydrofuranyl, pyrazolidinyl, imidazolidinyl, piperidinyl, piperazinyl or morpholinyl.

Aryl is preferably phenyl, tolyl, xylyl, mesityl, naphthyl, anthracenyl, phenanthrenyl or naphthacenyl, in particular phenyl or naphthyl.

Substituted aryl radicals preferably bear 1, 2, 3, 4 or 5, in particular 1, 2 or 3, substituents selected from among alkyl, alkoxy, carboxyl, carboxylate, trifluoromethyl, $—SO_3H$, sulfonate, $NE^1E^2$, alkylene-$NE^1E^2$, nitro, cyano and halogen.

Hetaryl is preferably pyrrolyl, pyrazolyl, imidazolyl, indolyl, carbazolyl, pyridyl, quinolinyl, acridinyl, pyridazinyl, pyrimidinyl and pyrazinyl.

Substituted hetaryl radicals preferably bear 1, 2 or 3 substituents selected from among alkyl, alkoxy, $—SO_3H$, sulfonate, $NE^1E^2$, alkylene-$NE^1E^2$, trifluoromethyl and halogen.

What has been said above with regard to alkyl, cycloalkyl and aryl radicals applies analogously to alkoxy, cycloalkyloxy and aryloxy radicals.

The radicals $NE^1E^2$, $NE^4E^5$ and $NE^7E^8$ are each preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is preferably fluorine, chlorine, bromine or iodine, preferably fluorine, chlorine or bromine.

For the purposes of the present invention, carboxylate and sulfonate are preferably derivatives of a carboxylic acid function and a sulfonic acid function, respectively, in particular a metal carboxylate or sulfonate, a carboxylic ester or sulfonic ester function or a carboxamide or sulfonamide function, particularly preferably an ester function. Such functions include, for example, esters of $C_1$–$C_4$-alkanols such as methanol, ethanol, n-propanol, isopropanol, n-butanol, sec-butanol and tert-butanol.

$M^+$ is an cation equivalent, i.e. a monovalent cation or the part of a polyvalent cation corresponding to a single positive charge. $M^+$ is preferably a cation such as $Li^+$, $Na^+$, $K^+$ or $NH_4^+$, $X^-$ is an anion equivalent, i.e. a monovalent anion or the part of a polyvalent anion corresponding to a single negative charge. $X^-$ is preferably an anion such as $F^-$, $Cl^-$ or $Br^-$.

x and y are each preferably an integer from 2 to 100.

$Y^1$ and $Y^2$ are preferably selected independently from among phosphine, phosphinite, phosphonite and phosphite radicals.

Preference is given to $Y^1$ and $Y^2$ each being, independently of one another, a radical of the formula $PR^7R^8$, $OPR^7R^8$, $P(OR^7)R^8$, $P(OR^7)(OR^8)$, $OP(OR^7)R^8$ or $OP(OR^7)(OR^8)$, where $R^7$ and $R^8$ are each, independently of one another, alkyl, cycloalkyl, heterocycloalkyl, aryl or hetaryl which may each bear one, two or three substituents selected from among alkyl, cycloalkyl, heterocycloalkyl, aryl, hetaryl, $COOR^k$,
$COO^-M^+$, $SO_3R^k$, $(SO_3)^-M^+$, $NE^4E^5$, alkylene-$NE^4E^5$, $NE^4E^5E^{6+}X^-$, alkylene-$NE^4E^5E^{6+}X^-$, $OR^k$, $SR^k$, $(CHR^lCH_2P)_yR^k$, $(CH_2N(E^4))_yR^k$, $(CH_2CH_2N(E^4))_yR^k$, halogen, trifluoromethyl, nitro, acyl and cyano, where, $R^k$, $E^4$, $E^5$ and $E^6$ are identical or different radicals selected from among hydrogen, alkyl, cycloalkyl and aryl, $R^1$ is hydrogen, methyl or ethyl, $M^+$ is a cation, $X^-$ is an anion and y is an integer from 1 to 120, or $R^7$ and $R^8$ together with the phosphorus atom and any oxygen atom(s) to which they are bound form a 5- to 8-membered heterocycle which may additionally be fused with one, two or three cycloalkyl, heterocycloalkyl, aryl or hetaryl groups, where the heterocycle and any fused-on groups present may each, independently of one another, bear one, two, three or four substituents selected from among alkyl, cycloalkyl, heterocycloalkyl, aryl, hetaryl, $COOR^k$, $COO^-M^+$, $SO_3R^k$, $SO^-_3M^+$, $NE^4E^5$, alkylene-$NE^4E^5$, $NE^4E^5E^{6+}X^-$, alkylene-$NE^4E^5E^{6+}X^-$, $OR^k$, $SR^k$, $(CHR^lCH_2O)_yR^k$, $(CH_2N(E^4))_yR^k$, $(CH_2CH_2N(E^4))_yR^k$, halogen, trifluoromethyl, nitro, acyl and cyano, where $R^k$, $R^l$, $E^4$, $E^5$, $E^6$, $M^+$, $X^-$ and y are as defined above.

In a preferred embodiment, one of the radicals $Y^1$ or $Y^2$ in the formula I is or both radicals $Y^1$ and $Y^2$ are selected from among radicals of the formulae $PR^7R^8$, $OPR^7R^8$, $P(OR^7)R^8$, $P(OR^7)(OR^8)$, $OP(OR^7)R^8$ and $OP(OR^7)(OR^8)$, where $R^7$ and $R^8$ together with the phosphorus atom and any oxygen atom(s) to which they are bound may form of a 5- to 8-membered heterocycle which may additionally be fused with one, two or three cycloalkyl, heterocycloalkyl, aryl and/or hetaryl groups, where the heterocycle and/or the fused-on groups may each bear, independently of one another, one, two, three or four substituents selected from among alkyl, alkoxy, halogen, nitro, cyano, carboxyl, $SO_3H$, sulfonate, $NE^3E^4$, alkylene-$NE^3E^4$ and carboxylate.

The radicals $Y^1$ and $Y^2$ are preferably selected from among radicals of the formula II

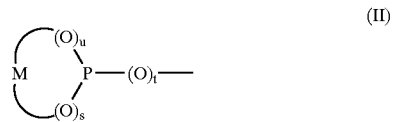

where s, t and u are each, independently of one another, 0 or 1,

M together with the phosphorus atom and any oxygen atom(s) to which it is bound forms a 5- to 8-membered heterocycle which may additionally be fused with one, two or three cycloalkyl, heterocycloalkyl, aryl and/or hetaryl groups, where the fused-on groups may each bear, independently of one another, one, two, three or four substituents selected from among alkyl, alkoxy, halogen, $SO_3H$, sulfonate, $NE^3E^4$, alkylene-$NE^3E^4$, nitro, cyano, carboxyl and carboxylate, and/or M may bear one, two or three substituents selected from among alkyl, alkoxy, substituted or unsubstituted cycloalkyl and substituted or unsubstituted aryl, and/or M may be interrupted by 1, 2 or 3 substituted or unsubstituted heteroatoms.

The radical M is preferably a $C_2$–$C_6$-alkylene bridge which is fused with one or two aryl groups and/or may bear a substituent selected from among alkyl, substituted or unsubstituted cycloalkyl and substituted or unsubstituted aryl and/or may be interrupted by a substituted or unsubstituted heteroatom.

Aryls fused onto the radicals M are preferably benzene or naphthalene. Fused-on beanzene rings are preferably unsubstituted or bear 1, 2 or 3, in particular 1 or 2, substituents selected from among alkyl, alkoxy, halogen, $SO_3H$, sulfonate, $NE^3E^4$, alkylene-$NE^3E^4$, trifluoromethyl, nitro, carboxyl, alkoxycarbonyl, acyl and cyano. Fused-on naphthalenes are preferably unsubstituted or bear 1, 2 or 3, in particular 1 or 2, of the substituents mentioned above for the fused-on benzene rings in the ring which is not fused on and/or in the fused-on ring. In the case of the substituents on the fused-on aryls, alkyl is preferably $C_1$–$C_4$-alkyl, in particular methyl, isopropyl and tert-butyl. Alkoxy is preferably $C_1$–$C_4$-alkoxy, in particular methoxy. Alkoxycarbonyl is preferably $C_1$–$C_4$-alkoxycarbonyl. Halogen is particularly preferably fluorine or chlorine.

If the $C_2$–$C_6$-alkylene bridge of the radical M is interrupted by 1, 2 or 3 substituted or unsubstituted heteroatoms, these are preferably selected from among O, S and $NR^m$, where $R^m$ is alkyl, cycloalkyl or aryl. The $C_2$–$C_6$-alkylene bridge of the radical M is preferably interrupted by a substituted or unsubstituted heteroatom.

If the $C_2$–$C_6$-alkylene bridge of the radical M is substituted, it preferably bears 1, 2 or 3, in particular 1, substituent(s) selected from among alkyl, cycloalkyl and aryl, where the aryl substituent may bear 1, 2 or 3 of the substituents mentioned for aryl. The alkylene bridge M preferably bears one substituent selected from among methyl, ethyl, isopropyl, phenyl, p-($C_1$–$C_4$-alkyl)phenyl, preferably p-methylphenyl, p-($C_1$–$C_4$-alkoxy)phenyl, preferably p-methoxyphenyl, p-halophenyl, preferably p-chlorophenyl, and p-trifluoromethylphenyl.

The radical M is preferably a $C_3$–$C_6$-alkylene bridge which is fused and/or substituted and/or interrupted by substituted or unsubstituted heteroatoms as described above. In particular, the radical M is a $C_3$–$C_6$-alkylene bridge which is fused with one or two benzene and/or naphthalene units which may bear 1, 2 or 3, in particular 1 or 2, of the abovementioned substituents.

Preference is given to the radical M (i.e. $R^7$ and $R^8$ together) together with the phosphorus atom and the oxygen atom(s) to which it is bound forming a 5- to 8-membered heterocycle and M ($R^7$ and $R^8$ together) being a radical selected from among radicals of the formulae III.1 to III.5,

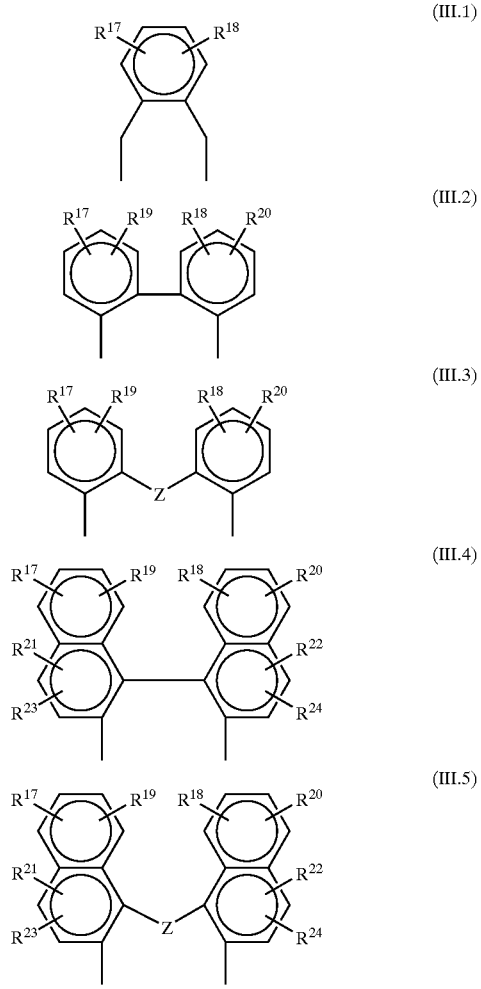

where
- Z is O, S or $NR^m$, where
  $R^m$ is alkyl, cycloalkyl or aryl,
  or Z is a $C_1$–$C_3$-alkylene bridge which may contain a double bond and/or bear an alkyl, cycloalkyl or aryl substituent, where the aryl substituent may in turn bear one, two or three of the substituents mentioned for aryl,
  or Z is a $C_2$–$C_3$-alkylene bridge which is interrupted by O, S or $NR^m$, and
- $R^{17}$, $R^{18}$, $R^{19}$, $R^{20}$, $R^{21}$, $R^{22}$, $R^{23}$ and $R^{24}$ are selected independently from among hydrogen, alkyl, cycloalkyl, aryl, alkoxy, cycloalkoxy, aryloxy, acyl, halogen, $SO_3H$, sulfonate, $NE^3E^4$, alkylene-$NE^3E^4$, trifluoromethyl, nitro, alkoxycarbonyl, carboxyl uad cyano,
- where $E^3$ and $E^4$ may be identical or different and are each alkyl, cycloalkyl or aryl.

In a further preferred embodiment, one of the radicals $Y^1$ and $Y^2$ in the formula I is or both radicals $Y^1$ and $Y^2$ are selected from among radicals of the formulae $PR^7R^8$, $OPR^7R^8$, $P(OR^7)R^8$, $P(OR^7)(OR^8)$, $OP(OR^7)R^8$ and $OP(OR^7)(OR^8)$, where the radicals $R^7$ and $R^8$ are not connected by a bridge. $R^7$ and $R^8$ are each, independently of one another, alkyl, cycloalkyl, aryl or hetaryl, where the aryl and hetaryl groups may each bear one, two or three substituents selected from among alkyl, cycloalkyl, aryl, alkoxy, cycloalkoxy, aryloxy, acyl, halogen, trifluoromethyl, nitro, cyano, carboxyl, alkoxycarbonyl and $NE^4E^5$, where $E^4$ and $E^5$ may be identical or different and are each alkyl, cycloalkyl or aryl.

$A^1$ is preferably O, S, $NR^c$ or $SiR^dR^e$, where the radicals $R^c$, $R^d$ and $R^e$ are as defined above.

Preference is given to $A^1$ being a radical of the formula $CR^fR^g$, where $R^f$ and $R^g$ are each, independently of one another, hydrogen, $C_1$–$C8$-alkyl, in particular $C_1$–$C_4$-alkyl, $C_5$–$C_8$-cycloalkyl, $C_5$–$C8$-heterocycloalkyl, aryl or hetaryl.

If $R^f$ and/or $R^g$ are alkyl radicals, these may bear one, two or three substituents selected from among cycloalkyl, heterocycloalkyl, aryl, hetaryl, $COOR^o$, $COO^-M^+$, $SO_3R^o$, $(SO_3)^-M^+$, $NE^7E^8$, alkylene-$NE^7E^8$, $NE^7E^8E^{9+}X^-$, alkylene-$NE^7E^8E^{9-}X^-$, $OR^o$, $SR^o$, $(CHR^pCH_2O)_zR^o$, $(CH_2N(E^7))_zR^o$, $(CH_2CH_2N(E^7))_zR^o$, halogen, trifluoromethyl, nitro, acyl and cyano, where $R^o$, $E^7$, $E^8$ and $E^9$ are identical or different radicals selected from among hydrogen, alkyl, cycloalkyl or aryl, $R^p$ is hydrogen, methyl or ethyl, $M^+$ is a cation equivalent, $X^-$ is an anion equivalent and z is an integer from 1 to 120.

If $R^f$ and/or $R^g$ are alkyl radicals, they may, regardless of the number of carbon atoms present in them, contain one, two or three double bonds and/or be fused with one, two or three cycloalkyl, heterocycloalkyl, aryl or hetaryl groups, where the fused-on groups each bear, independently of one another, one, two, three or four substituents selected from among alkyl and the substituents mentioned above for alkyl radicals $R^f$ and $R^g$.

If $R^f$ and/or $R^g$ are cycloalkyl, heterocycloalkyl, aryl or hetaryl, they may bear one, two or three substituents selected from among alkyl and the substituents mentioned above for alkyl substituents $R^f$ and/or $R^g$.

If $R^f$ and/or $R^g$ are cycloalkyl, heterocycloalkyl, aryl or hetaryl, these may be parts of a fused ring system containing 1, 2, 3 or 4 rings.

The group $A^1$ is preferably selected from among groups of the formulae IV.1 to IV.11

(IV.1)

(IV.2)

(IV.3)

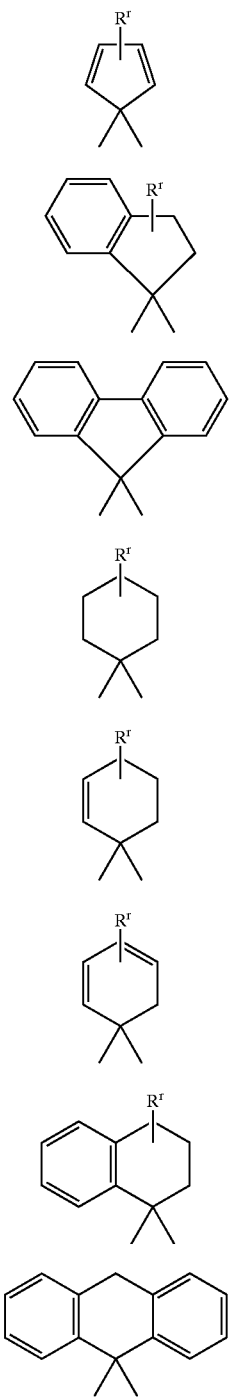

where
- $R^f$ and $R^g$ are each, independently of one another, $C_1$–$C_4$-alkyl, in particular methyl, and
- $R^r$ is selected from among alkyl, cycloalkyl, heterocycloalkyl, aryl, hetaryl, alkoxy, cycloalkyloxy, aryloxy, acyl, carboxyl, alkoxycarbonyl, hydroxy, nitro, cyano, trifluoromethyl, oxo and the ketals thereof and $NE^7E^8$, where $E^7$ and $E^8$ may be identical or different and are each alkyl, cycloalkyl or aryl.

The radicals $R^a$ and $R^b$ are preferably selected from among $C_1$–$C_8$-alkyl radicals, particularly preferably $C_1$–$C_4$-alkyl radicals. $R^a$ and $R^b$ are preferably methyl, ethyl, n-propyl, n-butyl or tert-butyl.

The radicals $R^1$, $R^2$, $R^3$, $R^4$, $R^5$ and $R^6$ are preferably selected from among hydrogen, alkyl, cycloalkyl, aryl and hetaryl. Preference is given to $R^1$ and $R^3$ being hydrogen and $R^2$ and $R^4$ being $C_1$–$C_4$-alkyl, e.g. methyl, ethyl, n-propyl, n-butyl or tert-butyl.

It is preferred that at least one of the radicals $R^1$, $R^2$, $R^3$, $R^4$, $R^5$ and/or $R^6$ is a polar (hydrophilic) group, which generally results in water-soluble catalysts. The polar groups are preferably selected from among $COOR^h$, $COO^-M^+$, $SO_3Rh$, $(SO_3)^-M^+$, $NE^1E^2$, alkylene-$NE^1E^2$, $NE^1E^2E^{3+}X^-$, alkylene-$NE^1E^2E^{3+}X^-$, $OR^h$, $SR^h$, $(CHR^iCH_2O)_xR^h$ or $(CH_2CH_2N(E^1))_xR^h$, where $R^h$, $R^i$, $E^1$, $E^2$, $E^3$, $M^+$, $X^-$ and x are as defined above.

$R^1$, $R^2$, $R^3$, $R^4$, $R^5$ and $R^6$ are particularly preferably hydrogen.

If $R^1$ and $R^2$ and/or $R^3$ and $R^4$ are a fused-on ring system, they are preferably benzene or naphthalene rings. Fused-on benzene rings are preferably unsubstituted or bear 1, 2 or 3, in particular 1 or 2, substituents selected from among alkyl, alkoxy, halogen, $SO_3H$, sulfonate, $NE^4E^5$, alkylene-$NE^4E^5$, trifluoromethyl, nitro, carboxyl, alkoxycarbonyl, acyl and cyano. Fused-on naphthalenes are preferably unsubstituted or bear 1, 2 or 3, in particular 1 or 2, of the substituents mentioned above for the fused-on benzene rings in the ring which is not fused on and/or in the fused-on ring.

In a preferred embodiment of the process of the present invention, use is made of a hydroformylation catalyst in which the compound of the formula I is selected from among compounds of the formulae I.1 to I.4

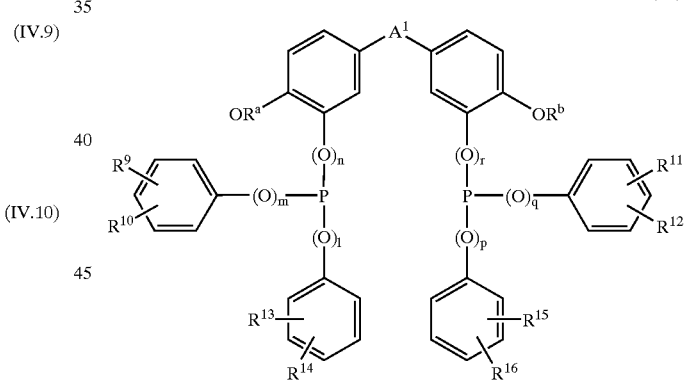

(I.1)

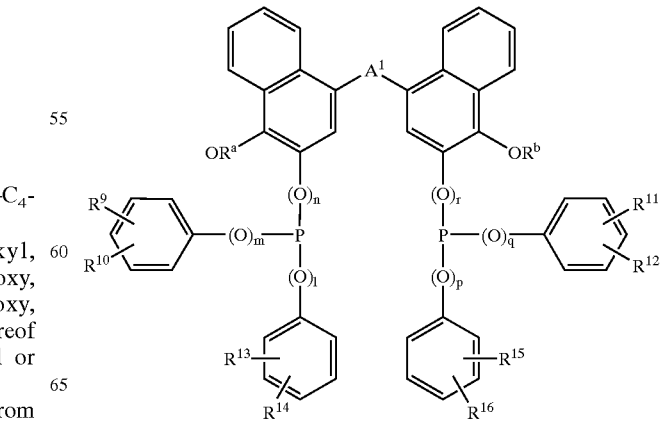

(I.2)

(I.3)

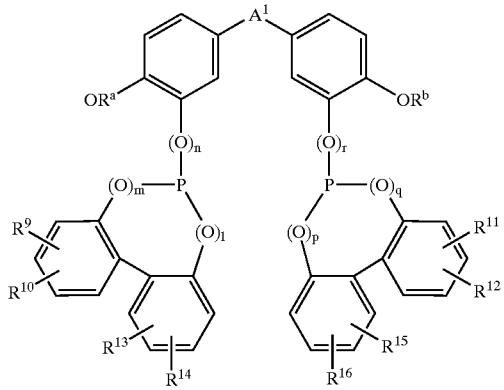

(I.4)

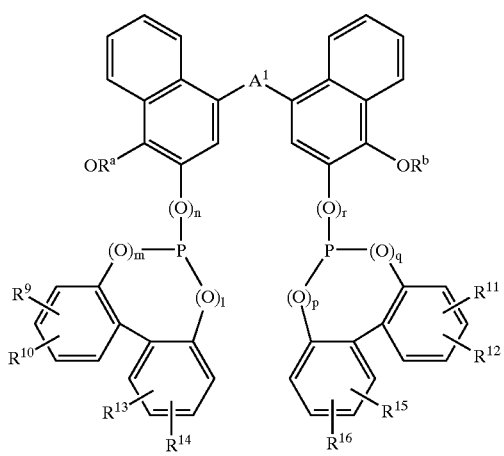

where

A$^1$ is O, S, NR$^c$, SiR$^d$R$^e$ or CR$^f$R$^g$, where

R$^c$, R$^d$, R$^e$, R$^f$ and R$^g$ are each, independently of one another, hydrogen, C$_1$–C$_6$-alkyl, C$_5$–C$_8$-cycloalkyl or phenyl, where R$^f$ and R$^g$ together with the carbon atom to which they are bound may also form a 5- to 8-membered heterocycle which may additionally be fused with one or two aryl groups, R$^a$ and R$^b$ are each, independently of one another, hydrogen or C$_1$–C$_6$-alkyl, R$^9$, R$^{10}$, R$^{11}$, R$^{12}$, R$^{13}$, R$^{14}$, R$^{15}$ and R$^{16}$ are selected independently from among hydrogen, alkyl, cycloalkyl, aryl, alkoxy, cycloalkoxy, aryloxy, acyl, halogen, trifluoromethyl, nitro, cyano, carboxyl, alkoxycarbonyl and NE$^3$E$^4$, where E$^3$ and E$^4$ may be identical or different and are each alkyl, cycloalkyl or aryl, and l, m, n, p, q and r are each, independently of one another 0 or 1.

The invention further provides compounds of the formula I

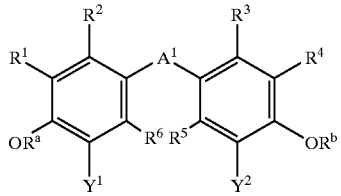

where

A$^1$ is O, S, NR$^c$, SiR$^d$R$^e$ or CR$^f$R$^g$, where

R$^c$, R$^d$, R$^e$, R$^f$ and R$^g$ are each, independently of one another, hydrogen, alkyl, cycloalkyl, heterocycloalkyl, aryl or hetaryl, where R$^f$ and R$^g$ together with the carbon atom to which they are bound may also form a 3- to 8-membered carbocycle or heterocycle which may additionally be fused with one, two or three cycloalkyl, heterocycloalkyl, aryl and/or hetaryl groups, Y$^1$ and Y$^2$ are, independently of one another, radicals containing at least one phosphorus atom, R$^a$ and R$^b$ are, independently of one another, hydrogen, alkyl, cycloalkyl, heterocycloalkyl, aryl, hetaryl or (CHR$^i$CH$_2$O)$_x$R$^h$, where R$^h$ is hydrogen, alkyl, cycloalkyl or aryl, R$^i$ is hydrogen, methyl or ethyl and x is an integer from 1 to 120, and R$^1$, R$^2$, R$^3$, R$^4$, R$^5$ and R$^6$ are each, independently of one another, hydrogen, alkyl, cycloalkyl, heterocycloalkyl, aryl, hetaryl, COOR$^h$, COO$^-$M$^+$, SO$_3$R$^h$, (SO$_3$)$^-$M$^+$, NE$^1$E$^2$, NE$^1$E$^2$E$^{3+}$X$^-$, alkylene-NE$^1$E$^2$E$^{3+}$X$^-$, OR$^h$, SR$^h$, (CHR$^i$CH$_2$O)$_x$R$^h$, (CH$_2$N(E$^1$))$_x$R$^h$, (CH$_2$CH$_2$N(E$^1$))$_x$R$^h$, halogen, trifluoromethyl, nitro, acyl or cyano, where R$^h$, E$^1$, E$^2$ and E$^3$ are identical or different radicals selected from among hydrogen, alkyl, cycloalkyl and aryl, R$^i$ is hydrogen, methyl or ethyl, M$^+$ is a cation, X$^-$ is an anion and x is an integer from 1 to 120, or R$^1$ and R$^2$ and/or R$^3$ and R$^4$ together with the adjacent carbon atoms of the benzene ring to which they are bound form a fused ring system comprising 1, 2 or 3 further rings.

As regards preferred embodiments of compounds of the formula I, reference may be made to the details provided above in respect of the ligands of the formula I used in the hydroformylation process of the present invention.

The invention further provides a catalyst comprising at least one complex of a metal of transition group VIII with at least one novel compound of the formula I as defined above.

The catalysts of the invention and used according to the invention may contain one or more of the compounds of the formula I as ligand. In addition to the above-described ligands of the formula I, they may further comprise at least one additional ligand selected from among halides, amines, carboxylates, acetylacetonate, arylsulfonates and alkylsulfonates, hydride, CO, olefins, dienes, cycloolefins, nitriles, N-containing heterocycles, aromatics and heteroaromatics, ethers, PF$_3$, phospholes, phosphabenzenes and monodentate, bidentate and polydentate phosphine, phosphinite, phosphonite, phosphoramidite and phosphite ligands.

The metal of transition group VIII is preferably cobalt, ruthenium, rhodium, palladium, platinum, osmium or iridium, in particular cobalt, rhodium, ruthenium or iridium.

The preparation of the compounds of the formula I of the invention and used according to the invention can start out from, for example, a compound of the formula I.a

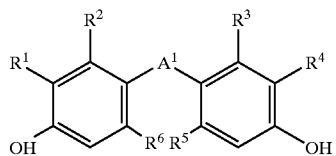

where
$A^1$, $R^1$, $R^2$, $R^3$, $R^4$, $R^5$ and $R^6$ are as defined above.

The functionalization of the hydroxyl groups to form the radicals $OR^a$ and $OR^b$ can be carried out by customary methods known to those skilled in the art. These include, for example, alkylation using customary alkylating agents such as methyl bromide, methyl iodide, dimethyl sulfate etc. They also include alkoxylation using alkylene oxides such as ethylene oxide, propylene oxide, butylene oxide and mixtures thereof.

The introduction of the phosphorus-containing group in the ortho position relative to $R^a$ and $R^b$ is carried out by "ortho-lithiation". Such reactions are described in the literature (cf., for example, D. W. Slocum, J. Org. Chem., 1976, 41, 3652–3654; J. M. Mallan, R. L. Bebb, Chem. Rev., 1969, 693 ff; V. Snieckus, Chem. Rev., 1980, 6, 879–933). The organolithium compounds obtained in this way can then be reacted with phosphorus-halogen compounds which bear a halogen atom, preferably a chlorine atom, on the phosphorus atom, for example a compound of the formula $Cl-P(O^sR^7)(O^uR^8)$, where s and u are 0 and 1. The novel compounds I in which $Y^1$ and $Y^2$ are each $PR^7R^8$, $P(OR^7)R^8$ or $P(OR^7)(OR^8)$, where $R^7$ and $R^8$ together with the phosphorus atom and any oxygen atom(s) to which they are bound may form a 5- to 8-membered heterocycle, are prepared by, for example, reaction of the alkylation or alkoxylation products of I.a with compounds of the formula II.a according to the following scheme,

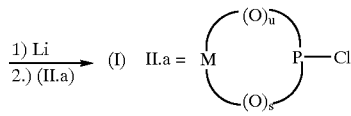

where M, s and u are as defined above.

In general, the catalysts or catalyst precursors used in each case are converted under hydroformylation conditions into catalytically active species of the formula $H_xM_y(CO)_zL_q$, where M is a metal of transition group VIII, L is a phosphorus-containing compound of the formula I and q, x, y, z are integers which depend on the valence and type of the metal and on the number of coordination sites occupied by the ligand L. It is preferred that z and q each have, independently of one another, a value of at least 1, e.g. 1, 2 or 3. The sum of z and q is preferably from 2 to 5. If desired, the complexes may further comprise at least one of the above-described additional ligands.

In a preferred embodiment, the hydroformylation catalysts are prepared in situ in the reactor used for the hydroformylation reaction. However, the catalysts of the present invention can, if desired, also be prepared separately and isolated by customary methods. For the in-situ preparation of the catalysts of the present invention, it is possible, for example, to react at least one compound of the formula I, a compound or a complex of a metal of transition group VIII, if desired at least one further ligand and, if appropriate, an activating agent in an inert solvent under the hydroformylation conditions.

Suitable rhodium compounds or complexes are, for example, rhodium(II) and rhodium(III) salts such as rhodium(III) chloride, rhodium(III) nitrate, rhodium(III) sulfate, potassium rhodium sulfate, rhodium(II) and rhodium(III) carboxylates, rhodium(II) or rhodium(III) acetate, rhodium(III) oxide, salts of rhodic(III) acid, trisammonium hexachlororhodate(III), etc. Also suitable are rhodium complexes such as dicarbonylrhodium acetylacetonate, acetylacetonatobisethylenerhodium(I), etc. Preference is given to using dicarbonylrhodium acetylacetonate or rhodium acetate.

Likewise suitable are ruthenium salts or compounds. Suitable ruthenium salts are, for example, ruthenium(III) chloride, ruthenium(IV), ruthenium(VI) or ruthenium(VIII) oxide, alkali metal salts of ruthenium oxo acids such as $K_2RuO_4$ or $KRuO_4$ or complexes such as $RuHCl(CO)(PPh_3)_3$. It is also possible to use the carbonyls of ruthenium, for example dodecacarbonyltriruthenium or octadecacarbonylhexaruthenium or mixed forms in which CO is partly replaced by ligands of the formula $PR_3$, e.g. $Ru(CO)_3(PPh_3)_2$, in the process of the present invention.

Suitable cobalt compounds are, for example, cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthanoate, and also the cobalt-caprolactamate complex. Here too, the carbonyl complexes of cobalt such as octacarbonyldicobalt, dodecacarbonyltetracobalt and hexadecacarbonylhexacobalt can be used.

The abovementioned and further suitable compounds of cobalt, rhodium, ruthenium and iridium are known in principle and are adequately described in the literature or can be prepared by a person skilled in the art by methods analogous to those for the known compounds.

Suitable activating agents are, for example, Brönsted acids, Lewis acids, e.g. $BF_3$, $AlCl_3$, $ZnCl_2$, and Lewis bases.

As solvents, preference is given to using the aldehydes formed in the hydroformylation of the respective olefins and also their higher-boiling downstream reaction products, e.g. the products of aldol condensation. Aromatics such as toluene and xylenes, hydrocarbons or mixtures of hydrocarbons are likewise suitable as solvents, including their use for dilution of the abovementioned aldehydes and the downstream products of the aldehydes. Further possible solvents are esters of aliphatic carboxylic acids with alkanols, for example ethyl acetate or Texanol™, ethers such as tert-butyl methyl ether and tetrahydrofuran. In the case of ligands which are sufficiently hydrophilic, it is also possible to use alcohols such as methanol, ethanol, n-propanol, isopropanol, n-butanol, isobutanol, ketones such as acetone and methyl ethyl ketone etc. Furthermore, "ionic liquids" can also be used as solvents. These are liquid salts, for example N,N'-di-alkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)-phosphonium salts, e.g. the tetrafluoroborates, acetates, tetrachloroaluminates, hexafluorophosphates, chlorides and tosylates.

It is also possible to carry out the reactions in water or aqueous solvent systems comprising water together with a water-miscible solvent, for example an alcohol such as methanol, ethanol, n-propanol, isopropanol, n-butanol, isobutanol, a ketone such as acetone or methyl ethyl ketone or another solvent. For this purpose, use is made of ligands of the formula I which are modified with polar groups, for example ionic groups such as $SO_3Me$, $CO_2Me$ where Me=Na, K or $NH_4$ or $N(CH_3)_{3+}$. The reactions then occur as a two-phase catalysis with the catalyst being present in the aqueous phase and the starting materials and products forming the organic phase. The reaction in the "ionic liquids" can also be carried out as a two-phase catalysis.

The molar ratio of phosphorus-containing ligand to metal of transition group VIII is generally in a range from about 1:1 to 1000:1.

As substrates for the hydroformylation process of the present invention, it is in principle possible to use all compounds which contain one or more ethylenically unsaturated double bonds. These include, for example, olefins such as α-olefins, internal straight-chain and internal branched olefins. Suitable α-olefins are, for example, ethylene, propene, 1-butene, 1-pentene, 1-hexene, 1-heptene, 1-octene, 1-nonene, 1-decene, 1-undecene, 1-dodecene, etc.

Preferred branched, internal olefins are $C_4$–$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Further olefins suitable for the hydroformylation process are $C_5$–$C_8$-cycloalkenes such as cyclopentene, cyclohexene, cycloheptene, cyclooctene and derivatives thereof, e.g. their $C_1$–$C_{20}$-alkyl derivatives bearing from 1 to 5 alkyl substituents. Other olefins suitable for the hydroformylation process are vinylaromatics such as styrene, α-methylstyrene, 4-isobutyl-styrene, etc. Olefins suitable for the hydroformylation process of the present invention additionally include α,β-ethylenically unsaturated monocarboxylic and/or dicarboxylic acids, their esters, monoesters and amides, e.g. acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., $C_1$–$C_{20}$-alkenols, -alkenediols and -alkadienols, e.g. 2,7-octadien-1-ol. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclooctatriene and also homopolymers and copolymers of butadiene.

The unsaturated compound used for the hydroformylation is preferably selected from among internal linear olefins and olefin mixtures comprising at least one internal linear olefin. Preferred linear (straight-chain) internal olefins are $C_4$–$C_{20}$-olefins such as 2-butene, 2-pentene, 2-hexene, 3-hexene, 2-heptene, 3-heptene, 2-octene, 3-octene, 4-octene, etc. and mixtures thereof.

The hydroformylation process of the present invention is preferably carried out using an industrially available olefin mixture which comprises, in particular, at least one internal linear olefin. Such mixtures include, for example, the Ziegler olefins obtained by targeted ethene oligomerization in the presence of alkylaluminum catalysts. These olefins are essentially unbranched olefins having a terminal double bond and an even number of carbon atoms. Further suitable olefins are the olefins obtained by oligomerization of ethene in the presence of various catalyst systems, e.g. the predominantly linear α-olefins obtained in the presence of alkylaluminum chloride/titanium tetrachloride catalysts and the α-olefins obtained in the presence of nickel-phosphine complexes as catalysts in the Shell Higher Olefin Process (SHOP). Suitable industrially available olefin mixtures are also obtained in the dehydrogenation of appropriate petroleum fractions, e.g. kerosene fractions or diesel oil fractions. To convert paraffins, predominantly n-paraffins, into olefins, three main processes are employed:
thermal cracking (steam cracking),
catalytic dehydrogenation and
chemical dehydrogenation by chlorination and dehydrochlorination.

Thermal cracking leads predominantly to α-olefins, while the other variants produce olefin mixtures which generally have relatively large proportions of olefins containing an internal double bond. Further suitable olefin mixtures are the olefins obtained in metathesis and telomerization reactions. These include, for example, the olefins from the Phillips triolefin process, viz. a modified SHOP process comprising ethylene oligomerization, double bond isomerization and subsequent metathesis (etheneolysis).

Further industrial olefin mixtures which can be used in the hydroformylation process of the present invention may be selected from among dibutenes, tributenes, tetrabutenes, dipropenes, tripropenes, tetrapropenes, mixtures of butene isomers, in particular raffinate II, dihexenes, dimers and oligomers from the Dimersol® process of IFP, the Octol® process of Hüls, the Polygas process, etc.

Preference is given to a process in which the hydroformylation catalyst is prepared in situ by reacting at least one compound of the formula I, a compound or a complex of a metal of transition group VIII and, if desired, an activating agent in an inert solvent under the hydroformylation conditions.

The hydroformylation reaction can be carried out continuously, semicontinuously or batchwise.

Suitable reactors for a continuous process are known to those killed in the art and are described, for example, in Ullmanns Enzyklopädie der technischen Chemie, vol. 1, 3rd edition, 1951, p. 743 ff.

Suitable pressure-rated reactors are likewise known to those skilled in the art and are described, for example, in Ullmanns Enzyklopädie der technischen Chemie, vol. 1, 3rd edition, 1951, p. 769 ff. In general, the process of the present invention is carried out using an autoclave which may, if desired, be provided with a stirrer and an internal lining.

The composition of the synthesis gas comprising carbon monoxide and hydrogen used in the process of the present invention can vary within wide limits. The molar ratio of carbon monoxide to hydrogen is generally from about 5:95 to 70:30, preferably from about 40:60 to 60:40. Particular preference is given to using a molar ratio of carbon monoxide to hydrogen in the region of 1:1.

The temperature in the hydroformylation reaction is generally in a range from about 20 to 180° C., preferably from about 50 to 150° C. The reaction is generally carried out at the partial pressure of the reaction gas at the reaction temperature chosen. The pressure is generally in a range from about 1 to 700 bar, preferably from 1 to 600 bar, in particular from 1 to 300 bar. The reaction pressure can be varied as a function of the activity of the hydroformylation catalyst used according to the present invention. In general, the novel catalysts based on phosphorus-containing compounds permit a reaction in a low pressure range, for instance in the range from 1 to 100 bar.

The hydroformylation catalysts of the invention and used according to the invention can be separated from the product from the hydroformylation reaction by customary methods known to those skilled in the art and can generally be reused for the hydroformylation.

The above-described, novel catalysts which comprise chiral compounds of the formula I are suitable for enantioselective hydroformylation.

The above-described catalysts can also be immobilized in an appropriate manner, e.g. by fixing on a suitable support, e.g. glass, silica gel, synthetic resin, etc., by binding via functional groups suitable as anchor groups, by adsorption, by grafting, etc. They are then also suitable for use as solid state catalysts.

Surprisingly, the hydroformylation activity of catalysts based on ligands of the formula I is generally higher than the isomerization activity in respect of the formation of internal double bonds. The catalysts of the present invention and the catalysts used according to the present invention advantageously display a high selectivity to α-aldehydes or α-alcohols in the hydroformylation of α-olefins. In addition, good yields of α-aldehydes or α-alcohols, in particular n-aldehydes or n-alcohols, are also generally obtained in the hydroformylation of internal linear olefins (isomerizing hydroformylation). Furthermore, these catalysts generally have a high stability under the hydroformylation conditions, so that longer catalyst operating lives can be achieved when using them than when using catalysts known from the prior art and based on conventional chelating ligands. Furthermore, the catalysts of the present invention and used according to the present invention advantageously display a high activity, so that the corresponding aldehydes or alcohols are generally obtained in good yields. In the hydroformylation of α-olefins and also of internal, linear olefins, they additionally display a very low selectivity to the hydrogenation product of the olefin used (high aldehyde selectivity).

The invention further provides for the use of catalysts comprising at least one complex of a metal of transition group VIII with at least one compound of the formula I as described above for hydroformylation, hydrocyanation, carbonylation and hydrogenation.

The hydrocyanation of olefins is a further application of the catalysts of the present invention. The hydrocyanation catalysts of the present invention likewise comprise complexes of a metal of transition group VIII, in particular cobalt, nickel, ruthenium, rhodium, palladium, platinum, preferably nickel, palladium or platinum and very particularly preferably nickel. In general, the metal is present in the zero-valent state in the metal complex of the present invention. The preparation of the metal complexes can be carried out as described above for use as hydroformylation catalysts. The same applies to the in-situ preparation of the hydrocyanation catalysts of the present invention.

A nickel complex suitable for preparing a hydrocyanation catalyst is, for example, bis(1,5-cyclooctadiene)nickel(0).

If desired, the hydrocyanation catalysts can be prepared in situ in a manner analogous to the method described for the hydroformylation catalysts.

The present invention therefore further provides a process for preparing nitrites by catalytic hydrocyanation in the presence of at least one of the above-described catalysts of the present invention. Suitable olefins for the hydrocyanation are generally the olefins mentioned above as starting materials for the hydroformylation. A specific embodiment of the process of the present invention relates to the preparation of mixtures of monoolefinic $C_5$-mononitriles having nonconjugated C═C and C≡N bonds by catalytic hydrogenation of 1,3-butadiene or 1,3-butadiene-containing hydrocarbon mixtures and the isomerization/further reaction to saturated $C_6$-dinitriles, preferably adiponitrile, in the presence of at least one catalyst according to the present invention. When hydrocarbon mixtures are used for preparing monoolefinic $C_5$-mononitriles by the process of the present invention, preference is given to using a hydrocarbon mixture which has a 1,3-butadiene content of at least 10% by volume, preferably at least 25% by volume, in particular at least 40% by volume.

1,3-Butadiene-containing hydrocarbon mixtures are obtainable on an industrial scale. Thus, for example, petroleum refining by steam cracking of naphtha gives a hydrocarbon mixture known as $C_4$ fraction which has a high total olefin content, with about 40% being 1,3-butadiene and the remainder being made up of monoolefins and multiply unsaturated hydrocarbons and alkanes. These streams always also contain small amounts of generally up to 5% of alkynes, 1,2-dienes and vinylacetylene.

Pure 1,3-butadiene can be isolated from industrially available hydrocarbon mixtures by, for example, extractive distillation.

The catalysts of the present invention can be used advantageously for the hydrocyanation of such olefin-containing, in particular 1,3-butadiene-containing, hydrocarbon mixtures, generally without prior purification of the hydrocarbon mixture by distillation. Any olefins present which adversely affect the effectiveness of the catalysts, e.g. alkynes or cumulenes, can, if appropriate, be removed from the hydrocarbon mixture by selective hydrogenation prior to the hydrocyanation. Suitable methods of selective hydrogenation are known to those skilled in the art.

The hydrocyanation of the present invention can be carried out continuously, semicontinuously or batchwise. Suitable reactors for a continuous reaction are known to those skilled in the art and are described, for example, in Ullmanns Enzyklopädie der technischen Chemie, vol. 1, 3rd Edition, 1951, p. 743 ff. Preference is given to using a cascade of stirred vessels or a tube reactor for the continuous variant of the process of the present invention. Suitable reactors for the semicontinuous or continuous embodiment, which may be pressure-rated, are known to those skilled in the art and are described, for example, in Ullmanns Enzyklopädie der technischen Chemie, volume 1, 3rd Edition, 1951, p. 769 ff. In general, the process of the present invention is carried out using an autoclave which may, if desired, be provided with a stirrer and an internal lining.

The hydrocyanation catalysts of the present invention can be separated from the reaction mixture obtained from the hydrocyanation reaction by customary methods known to those skilled in the art and can generally be reused for the hydrocyanation.

The invention further provides a process for the carbonylation of compounds which contain at least one ethylenically unsaturated double bond by reaction with carbon monoxide and at least one compound containing a nucleophilic group in the presence of a carbonylation catalyst based on a ligand of the formula I.

The carbonylation catalysts of the present invention likewise comprise complexes of a metal of transition group VIII, preferably nickel, cobalt, iron, ruthenium, rhodium or palladium, in particular palladium. The preparation of the metal complexes can be carried out as described above in the case of the hydroformylation catalysts and the hydrocyanation catalysts. The same applies to the in-situ preparation of the carbonylation catalysts of the present invention.

Suitable olefins for the carbonylation are the olefins mentioned above in general terms as feedstocks for hydroformylation and hydrocyanation.

The compounds containing a nucleophilic group are preferably selected from among water, alcohols, thiols, carboxylic esters, primary and secondary amines.

A preferred carbonylation reaction is the conversion of olefins into carboxylic acids by means of carbon monoxide and water (hydrocarboxylation). This includes, in particular, the reaction of ethylene with carbon monoxide and water to form propionic acid.

The invention is illustrated by the following, nonrestrictive examples.

EXAMPLES

The following ligands were used for hydroformylation:

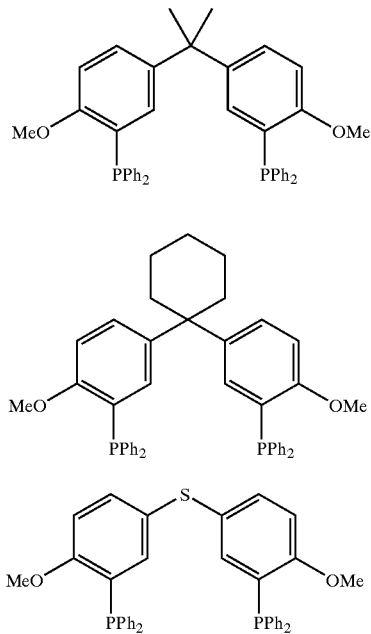

I. Preparation of the ligands
I.I Preparation of ligand I
Preparation of 2,2-bis(4-methoxyphenyl)propane 11.48 g (0.05 mol) of bisphenol A are dissolved in 100 ml of acetone, after which 27.69 g (0.2 mol) of $K_2CO_3$ and 0.88 g (2.38 mmol) of $NBu_4I$ are added to this solution. 21.69 g (0.15 mol) of methyl iodide are then added and the resulting suspension is refluxed while stirring vigorously. After a reaction time of 16 hours, the reaction mixture is allowed to cool, the solids are removed by filtration through a glass filter and the filtrate is poured into a mixture of 100 ml of diethyl ether and 100 ml of aqueous KOH (15% strength by weight). After extraction, the ether phase is isolated and washed with 75 ml of saturated sodium chloride solution and 75 ml of water. It is dried over $MgSO_4$, the desiccant is removed by filtration through Celite and the solvent is subsequently removed under reduced pressure, giving an oil. After addition of 50 ml of ethanol and removal of the ethanol, the product is obtained in the form of a powder. Yield: 9.44 g (73.2%).

Preparation of Ligand I 44.6 ml (0.11 mol) of a 2.5 molar solution of butyllithium in hexane are added to 12.95 g (0.11 mol) of tetramethylethylenediamine (TMEDA). The resulting mixture is stirred at 0° C. for one hour, subsequently cooled to −15° C. in an ice/sodium chloride bath and a solution of 13.29 g (0.052 mol) of 2,2-bis(4-methoxyphenyl)propane in 75 ml of diethyl ether is added dropwise over a period of 1.5 hours. The mixture is allowed to warm to room temperature- and is stirred overnight. The mixture is subsequently cooled to 0° C. and a mixture of 24.6 g (0.11 mol) of $ClP(C_6H_5)_2$ with 30 ml of hexane is added dropwise over a period of one hour. The mixture is allowed to warm to room temperature, stirred overnight, the solvent is removed under reduced pressure and 60 ml of dichloromethane are added. The resulting mixture is washed with 50 ml of saturated sodium chloride solution, and the organic phase is separated off and dried over $MgSO_4$. After filtration through Celite, the solvent is removed under reduced pressure to leave an oil which solidifies. The resulting solid is pulverized and 40 ml of ethanol are added, which results in a solution and a white precipitate. Removal of the solvent and a second extraction with ethanol gives the title compound. Yield: 17.46 g (54%).

II. Hydroformylations

Example 1

Hydroformylation of 1-octene Using Ligand I 8.1 mg of dicarbonylrhodium acetylacetonate and 287.9 mg of ligand I (100 ppm of Rh, ligand/metal ratio=15:1) were weighed out separately, each dissolved in 8 g of diphenyl ether, mixed and treated at 100° C. with a synthesis gas mixture of $CO/H_2$ (1:1) at 10 bar in a steel autoclave fitted with a sparging stirrer. After 120 minutes, the autoclave was depressurized, 16 g of 1-octene were then added and the 1-octene was hydroformylated at 100° C. and 10 bar for 4 hours. The conversion was 98%, the aldehyde selectivity was 98% and the proportion of α-products (n-nonanal and isononanal) was 99%.

Example 2

Hydroformylation of 1-octene Using Ligand II 8 mg of dicarbonylrhodium acetylacetonate and 324.1 mg of ligand II (98 ppm of Rh, ligand/metal ratio=15:1) were weighed out separately, each dissolved in 8 g of diphenyl ether, mixed and treated at 100° C. with a synthesis gas mixture of $CO/H_2$ (1:1) at 10 bar in a steel autoclave fitted with a sparging stirrer. After 30 minutes, the autoclave was depressurized, 16 g of 1-octene were then added and the 1-octene was hydroformylated at 100° C. and 10 bar for 4 hours. The conversion was 99%, the aldehyde selectivity was 98% and the proportion of α-products (n-nonanal and isononanal) was 99%.

Example 3

Hydroformylation of 1-octene Using Ligand III 0.9 mg of dicarbonylrhodium acetylacetonate and 22.4 mg of ligand III (60 ppm of Rh, ligand/metal ratio=10:1) were weighed out separately, each dissolved in 1.5 g xylene, mixed and treated at 100° C. with a synthesis gas mixture of $CO/H_2$ (1:1) at 10 bar in a steel autoclave fitted with a sparging stirrer. After 30 minutes, the autoclave was depressurized, 3 g of 1-octene were then added and the 1-octene was hydroformylated at 100° C. and 10 bar for 4 hours. The conversion was 98%, the aldehyde selectivity was 95% and the proportion of α-products (n-nonanal and isononanal) was 98%.

We claim:

1. A process for the hydroformylation of compounds containing at least one ethylenically unsaturated double bond by reaction with carbon monoxide and hydrogen in the presence of a hydroformylation catalyst comprising at least one complex of a metal of transition group VIII with at least one ligand selected from among compounds of the formula I

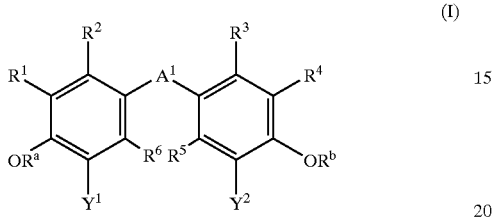

where
$A^1$ is O, S, $NR^c$, $SiR^dR^e$ or $CR^fR^g$, where
  $R^c$, $R^d$, $R^e$, $R^f$ and $R^g$ are each, independently of one another, hydrogen, alkyl, cycloalkyl, heterocycloalkyl, aryl or hetaryl, where $R^f$ and $R^g$ together with the carbon atom to which they are bound may also form a 3- to 8-membered carbocycle or heterocycle which may additionally be fused with one, two or three cycloalkyl, heterocycloalkyl, aryl and/or hetaryl groups, $Y^1$ and $Y^2$ are, independently of one another, radicals containing at least one phosphorus atom, $R^a$ and $R^b$ are, independently of one another, hydrogen, alkyl, cycloalkyl, heterocycloalkyl, aryl, hetaryl or $(CHR^iCH_2O)_xR^h$, where $R^h$ is hydrogen, alkyl, cycloalkyl or aryl, $R^i$ is hydrogen, methyl or ethyl and x is an integer from 1 to 120, and $R^1$, $R^2$, $R^3$, $R^4$, $R^5$ and $R^6$ are each, independently of one another, hydrogen, alkyl, cycloalkyl, heterocycloalkyl, aryl, hetaryl, $COOR^h$, $COO^-M^+$, $SO_3R^h$, $(SO_3)^-M^+$, $NE^1E^2$, $NE^1E^2E^{3+}X^-$, alkylene-$NE^1E^2E^{3+}X^-$, $OR^h$, $SR^h$, $(CHRiCH_2O)_xR^h$, $(CH_2N(E^1))_xR^h$, $(CH_2CH_2N(E^1))_xR^h$, halogen, trifluoromethyl, nitro, acyl or cyano, where
  $R^h$, $E^1$, $E^2$ and $E^3$ are identical or different radicals selected from among hydrogen, alkyl, cycloalkyl and aryl,
  $R^i$ is hydrogen, methyl or ethyl,
  $M^+$ is a cation,
  $X^-$ is an anion and
  x is an integer from 1 to 120, or $R^1$ and $R^2$ and/or $R^3$ and $R^4$ together with the adjacent carbon atoms of the benzene ring to which they are bound form a fused ring system comprising 1, 2 or 3 further rings.

2. A process as claimed in claim 1, wherein $Y^1$ and $Y^2$ in formula I are each, independently of one another, a radical of the formula $PR^7R^8$, $OPR^7R^8$, $P(OR^7)R^8$, $P(OR^7)(OR^8)$, $OP(OR^7)R^8$ or $OP(OR^7)(OR^8)$, where
  $R^7$ and $R^8$ are each, independently of one another, alkyl, cycloalkyl, heterocycloalkyl, aryl or hetaryl which may each bear one, two or three substituents selected from among alkyl, cycloalkyl, heterocycloalkyl, aryl, hetaryl, $COOR^k$, $COO^-M^+$, $SO_3R^k$, $(SO_3)^-M^+$, $NE^4E^5$, alkylene-$NE^4E^5$, $NE^4E^5E^{6+}X^-$, alkylene-$NE^4E^5E^{6+}X^-$, $OR^k$, $SR^k$, $(CHR^iCH_2O)_yR^k$, $(CH_2N(E^4))_yR^k$, $(CH_2CH_2N(E^4))_yR^k$, halogen, trifluoromethyl, nitro, acyl and cyano, where,
  $R^k$, $E^4$, $E^5$ and $E^6$ are identical or different radicals selected from among hydrogen, alkyl, cycloalkyl and aryl,
  $R^1$ is hydrogen, methyl or ethyl,
  $M^+$ is a cation,
  $X^-$ is an anion and
  y is an integer from 1 to 120, or $R^7$ and $R^8$ together with the phosphorus atom and any oxygen atom(s) to which they are bound form a 5- to 8-membered heterocycle which may additionally be fused with one, two or three cycloalkyl, heterocycloalkyl, aryl or hetaryl groups, where the heterocycle and any fused-on groups present may each, independently of one another, bear one, two, three or four substituents selected from among alkyl, cycloalkyl, heterocycloalkyl, aryl, hetaryl, $COOR^k$, $COO^-M^+$, $SO_3R^k$, $SO^-_3M^+$, $NE^4E^5$, alkylene-$NE^4E^5$, $NE^4E^5E^{6+}X^-$, alkylene-$NE^4E^5E^{6+}X^-$, $OR^k$, $SR^k$, $(CHR^lCH_2O)_yR^k$, $(CH_2N(E^4))_yR^k$, $(CH_2CH_2N(E^4))_yR^k$, halogen, trifluoromethyl, nitro, acyl and cyano, where $R^k$, $R^l$, $E^4$, $E^5$, $E^6$, $M^+$, $X^-$ and y are as defined above.

3. A process as claimed in claim 1, wherein the group $A^1$ is selected from among groups of the formula IV.1 to IV.11

 (IV.1)

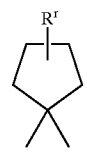 (IV.2)

 (IV.3)

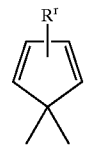 (IV.4)

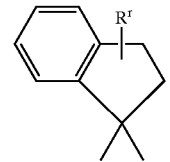 (IV.5)

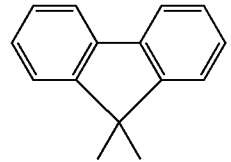 (IV.6)

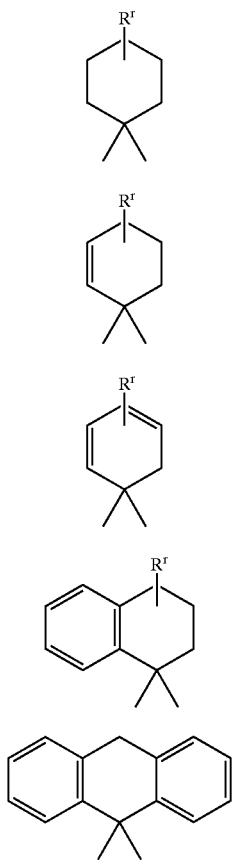

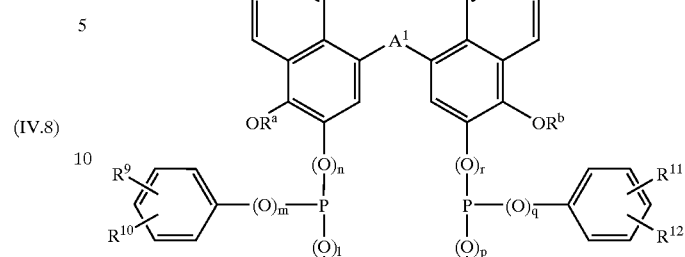

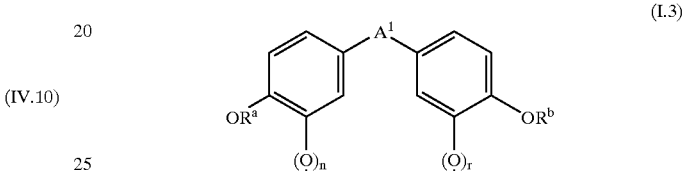

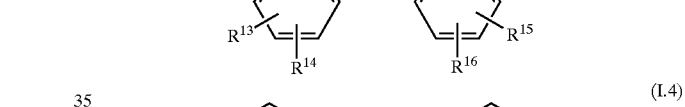

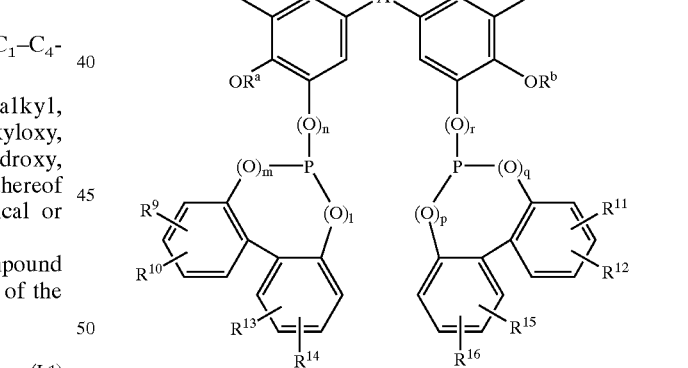

where

R$^f$ and R$^g$ are each, independently of one another, C$_1$–C$_4$-alkyl, in particular methyl and R$^r$ is selected from among alkyl, cycloalkyl, heterocycloalkyl, aryl, hetaryl, alkoxy, cycloalkyloxy, aryloxy, acyl, carboxyl, alkoxycarbonyl, hydroxy, nitro, cyano, trifluoromethyl, oxo and the ketals thereof and NE$^7$E$^8$, where E$^7$ and E$^8$ may be identical or different and are each alkyl, cycloalkyl or aryl.

4. A process as claimed in claim 1, wherein the compound of the formula I is selected from among compounds of the formulae I.1 to I.4

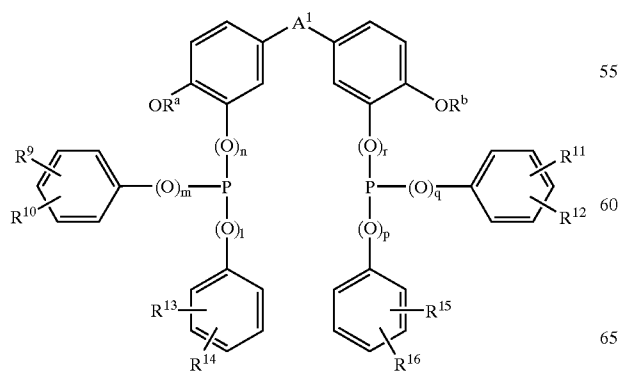

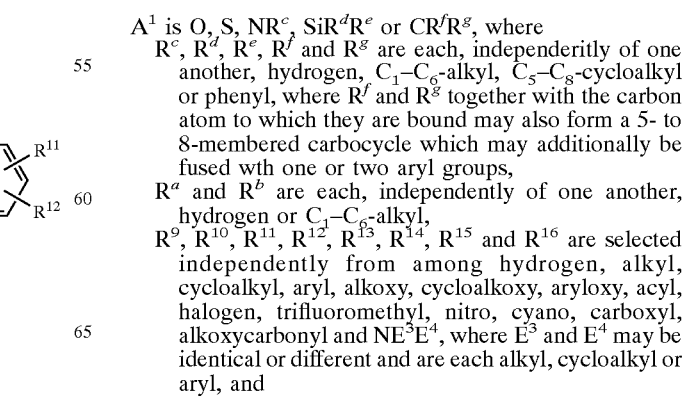

A$^1$ is O, S, NR$^c$, SiR$^d$R$^e$ or CR$^f$R$^g$, where

R$^c$, R$^d$, R$^e$, R$^f$ and R$^g$ are each, independently of one another, hydrogen, C$_1$–C$_6$-alkyl, C$_5$–C$_8$-cycloalkyl or phenyl, where R$^f$ and R$^g$ together with the carbon atom to which they are bound may also form a 5- to 8-membered carbocycle which may additionally be fused with one or two aryl groups, R$^a$ and R$^b$ are each, independently of one another, hydrogen or C$_1$–C$_6$-alkyl, R$^9$, R$^{10}$, R$^{11}$, R$^{12}$, R$^{13}$, R$^{14}$, R$^{15}$ and R$^{16}$ are selected independently from among hydrogen, alkyl, cycloalkyl, aryl, alkoxy, cycloalkoxy, aryloxy, acyl, halogen, trifluoromethyl, nitro, cyano, carboxyl, alkoxycarbonyl and NE$^3$E$^4$, where E$^3$ and E$^4$ may be identical or different and are each alkyl, cycloalkyl or aryl, and l, m, n, p, q and r are each, independently of one another 0 or 1.

5. A process as claimed in claim 1, wherein the metal of transition group VIII is selected from among cobalt, ruthenium, iridium, rhodium, palladium and platinum.

6. A process as claimed in claim 1, wherein the catalyst further comprises at least one additional ligand selected from among halides, amines, carboxylates, acetylacetonate, arylsulfonates and alkylsulfonates, hydride, CO, olefins, dienes, cycloolefins, nitriles, N-cpntaining heterocycles, aromatics and heteroaromatics, ethers PF$_3$, phospholes, phosphabenzenes and monodentate, bidentate and polydentate phosphine, phosphinite, phosphonite, phosphoramidite and phosphite ligands.

7. A process as claimed in claim 1, wherein the unsaturated compound used for the hydroformylation is selected from among internal linear olefins and olefins.

8. A compound of the formula I

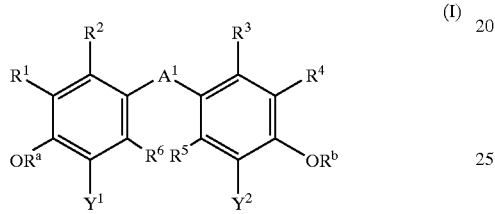

(I)

where
A$^1$ is O, S, NR$^c$, SiR$^d$R$^e$ or CR$^f$R$^g$, where
R$^c$, R$^d$, R$^e$, R$^f$ and R$^g$ are each, independently of one another, hydrogen, alkyl, cycloalkyl, heterocycloalkyl, aryl or hetaryl, where R$^f$ and R$^g$ together with the carbon atom to which they are bound may also form a 3- to 8-membered carbocycle or heterocycle which may additionally be fused with one, two or three cycloalkyl, heterocycloalkyl, aryl and/or hetaryl groups, Y$^1$ and Y$^2$ are, independently of one another, radicals containing at least one phosphorus atom, R$^a$ and R$^b$ are, independently of one another, hydrogen, alkyl, cycloalkyl, heterocycloalkyl, aryl, hetaryl or (CHR$^i$CH$_2$O)$_x$R$^h$, where R$^h$ is hydrogen, alkyl, cycloalkyl or aryl, R$^i$ is hydrogen, methyl or ethyl and x is an integer from 1 to 120, and R$^1$, R$^2$, R$^3$, R$^4$, R$^5$ and R$^6$ are each, independently of one another, hydrogen, alkyl, cycloalkyl, heterocycloalkyl, aryl, hetaryl, COOR$^h$, COO$^-$M$^+$, SO$_3$R$^h$, (SO$_3$)$^-$M$^+$, NE$^1$E$^2$, NE$^1$E$^2$E$^{3+}$X$^-$, alkylene-NE$^1$E$^2$E$^{3+}$X$^-$, OR$^h$, SR$^h$, (CHR$^i$CH$_2$O)$_x$R$^h$, (CH$_2$N(E$^1$))$_x$R$^h$, (CH$_2$CH$_2$N(E$^1$))$_x$R$^h$, halogen, trifluoromethyl, nitro, acyl or cyano, where R$^h$, E$^1$, E$^2$ and E$^3$ are identical or different radicals selected from among hydrogen, alkyl, cycloalkyl and aryl, R$^i$ is hydrogen, methyl or ethyl, M$^+$ is a cation, X$^-$ is an anion and x is an integer from 1 to 120, or R$^1$ and R$^2$ and/or R$^3$ and R$^4$ together with the adjacent carbon atoms of the benzene ring to which they are bound form a fused ring system comprising 1, 2 or 3 further rings.

9. A catalyst comprising at least one complex of a metal of transition group VIII with at least one ligand selected from among compounds of the formula I as defined in claim 8.

* * * * *

UNITED STATES PATENT AND TRADEMARK OFFICE
CERTIFICATE OF CORRECTION

PATENT NO. : 6,639,114 B2
DATED : October 28, 2003
INVENTOR(S) : Ahlers et al.

It is certified that error appears in the above-identified patent and that said Letters Patent is hereby corrected as shown below:

Title page,
Item [75], Inventors, "Eindhoven (DE)" should be -- Eindhoven (NL) --.

Column 21,
Line 42, "$(CHRiCH_2O)_xR^h$" should be -- $(CHR^iCH_2O)_xR^h$ --.

Column 24,
Line 54, "independeritly" should be -- independently --.

Column 25,
Line 9, "N-cpntaining" should be -- N-containing --.

Column 26,
Line 16, "$(CHRiCH_2O)_xR^h$" should be -- $(CHR^iCH_2O)_xR^h$ --.

Signed and Sealed this

Sixteenth Day of March, 2004

JON W. DUDAS
*Acting Director of the United States Patent and Trademark Office*